United States Patent
Pekkarinen et al.

(12)

(10) Patent No.: US 6,520,997 B1
(45) Date of Patent: Feb. 18, 2003

(54) POROUS THREE DIMENSIONAL STRUCTURE

(75) Inventors: Michael O. Pekkarinen, Lincolnshire, IL (US); James Brauker, Flagstaff, AZ (US)

(73) Assignee: Baxter International Inc., Deerfield, IL (US)

(*) Notice: Subject to any disclaimer, the term of this patent is extended or adjusted under 35 U.S.C. 154(b) by 0 days.

(21) Appl. No.: 09/731,486

(22) Filed: Dec. 7, 2000

Related U.S. Application Data

(60) Provisional application No. 60/169,714, filed on Dec. 8, 1999.

(51) Int. Cl.[7] .................................................. A61F 2/36
(52) U.S. Cl. ................................. 623/23.72; 623/23.74
(58) Field of Search ........................... 623/23.72, 23.74; 427/2.24

(56) References Cited

U.S. PATENT DOCUMENTS

| | | |
|---|---|---|
| 5,348,788 A | 9/1994 | White |
| 5,496,372 A | 3/1996 | Hamamoto et al. |
| 5,514,378 A | 5/1996 | Mikos et al. |
| 5,543,046 A | 8/1996 | Van Rijn |
| 5,653,687 A | 8/1997 | Mills et al. |
| 5,681,568 A | 10/1997 | Goldin et al. |
| 5,711,960 A | 1/1998 | Shikinami |
| 5,714,160 A | 2/1998 | Magruder et al. |
| 5,807,406 A | 9/1998 | Brauker et al. |
| 5,843,069 A | 12/1998 | Butler et al. |
| 5,876,452 A | 3/1999 | Athanasiou et al. |
| 5,891,728 A | 4/1999 | Wendel et al. |
| 5,938,923 A | 8/1999 | Tu et al. |
| 6,044,981 A | 4/2000 | Chu et al. |
| 6,333,029 B1 | 12/2001 | Vyakarnam et al. |

FOREIGN PATENT DOCUMENTS

WO     WO 98/13131     4/1998

OTHER PUBLICATIONS

Colton, "Implantable Biohybrid Artificial Organs", 4 Cell Transplant 415–36 (1995).

Spector et al., "The Local Tissue Response to Biomaterials", 5 Crit. Rev. Biocompat. 269–95 (1989).

Freeman et al., "Study of the Mass Transport Resistance of Glucose Across Rat Capsular Membranes", 110 Mater, Res. Soc. Symp. Proc. 773–78 (1989).

Brauker et al., "Neovascularization of Synthetic Membranes Directed by Membrane Microarchitecture", 29 J. Biomed. Mat. Res. 1517–24 (1995).

Padera et al., "Time Course of Membrane Microarchitecture–driven Neovascularization", 17 Biomaterials 277–84 (1996).

(List continued on next page.)

*Primary Examiner*—David J. Isabella
*Assistant Examiner*—Thomas C. Barrett
(74) *Attorney, Agent, or Firm*—Senniger, Powers, Leavitt & Roedel

(57) ABSTRACT

A porous three dimensional structure for implantation in a host animal capable of producing an inflammatory foreign body response. The structure includes first and second layers spaced by a plurality of posts having a predetermined length connecting the first and second layers. Each of the layers has a plurality of openings of a predetermined size permitting fluids and inflammatory cells of the animal to pass through the openings and migrate into an interior volume defined by the first and second layers. The size of the openings and length of the posts promote a non-flattened morphology of the cells. The structure promotes vascularization adjacent to the structure when implanted into the animal.

44 Claims, 5 Drawing Sheets

OTHER PUBLICATIONS

DeFife et al., "Cytoskeletal and Adhesive Structural Polarizations Accompany IL–13–induced Human Macrophage Fusion", 47 The Journal of Histochemical Society, Inc. 65–74 (1999).

DeFife et al., "Disruption of Filamentous Actin Inhibits Human Macrophage Fusion", 13 FASEB Journal 823–832 (1999).

Nelson et al., "Microfabrication of Porous Polyimide Membranes", 183rd meeting of The Electrochemical Society, Inc. (1993).

Beirne et al., "Microfabricated Polyimide Membrane Test Structures", publication title and date unknown.

Lukkassen, "An Investigation into the Causes of Pyrogenic Reactions in Haemodialysis and Haemodiafiltration Patients", Thesis submitted to Univ. of Oslo (1997).

Fennrich, "Detection of Endotoxins and Other Pyrogens Using Human Whole Blood", Development of Biological Standards (1999).

Hartung et al., "Detection of Pyrogens Using Humans Whole Blood", 9 In Vito Toxicology 353–359 (1996).

Poole et al., "Detection of Pyrogen by Cytokine Release", The Lancet 130 (Jan. 16, 1988).

Subkowski et al., "Monoclonal Antibodies Against Human Endothelin–Converting Enzyme–1", 19 Journal of Immunoassay 75–93 (1998).

Finch–Arietta et al., "Cytokine Production in Whole Blood ex vivo", 34 Agents and Actions 49–52 (1991).

Desch et al., "Production of Human Tumor Necrosis Factor from Whole Blood Ex Vivo", 8 Lymphokine Research 141–146 (1989).

Taktak, et al., "Assay of Pyrogens by Interleukin–6 Release from Monocytic Cell Lines", 43 J. Pharm. Pharamacol. 578–582 (1991).

POROUS THREE DIMENSIONAL STRUCTURE

CROSS-REFERENCE TO RELATED APPLICATION

This application claims priority from provisional U.S. application Ser. No. 60/169,714, filed Dec. 8, 1999, which is hereby incorporated by reference.

FIELD OF THE INVENTION

The present invention relates to porous, three dimensional structures for use in applications where a reduced foreign body capsule formation and increased adjacent vascularization is desired. Practical applications include membranes and coatings for devices to be implanted into animals.

BACKGROUND OF THE INVENTION

Implantable medical devices with biological components are used for various purposes, such as indwelling chemical sensors, controlled drug-release systems, and biohybrid artificial organs for use with cellular therapies. See, for example, Colton, *Implantable Biohybrid Artificial Organs*, 4 Cell Transplant 415–36 (1995). All of these devices have in common the need for adequate perfusion of small and large molecules to or from the blood stream through the surrounding soft tissue. A serious problem in the development of devices for these applications is the formation of an avascular fibrous capsule around the implanted device. The capsule consists of (i) a layer of macrophages and/or foreign body giant cells at the material-tissue interface, overlain by (ii) an avascular region up to 100 $\mu$m thick containing layers of fibroblasts embedded in a collagen matrix, which in turn is overlain by (iii) a region of blood vessels and fibroblasts in a loose connective tissue matrix. Spector, et al., *The Local Tissue Response to Biomaterials*, 5 Crit. Rev. Biocompat. 269–95 (1989). This capsule creates extra diffusion distance between the vasculature and the device. In addition, the tissue capsule may have inherently poor transport properties, as evidenced by measurements of glucose permeation through fibrotic tissue capsules formed on silicone rubber implanted subcutaneously in rats. The effective diffusion coefficient though this capsule is estimated to be one to two orders of magnitude lower than the value in water, Freeman, et al., *A Study of the Mass Transport Resistance of Glucose Across Rat Capsular Membranes*, 110 Mater. Res. Soc. Symp. Proc. 773–78 (1989). This reduced diffusion of nutrients and oxygen through the foreign body fibrous capsule has deleterious effects on the viability and/or function of tissues implanted in a biohybrid artificial organ.

Brauker discovered that certain microporous materials, when implanted subcutaneously, induce permanent neovascularization at the interface with host tissue by virtue of their morphology and microarchitecture. Brauker, et al., *Neovascularization of Synthetic Membranes Directed by Membrane Microarchitecture*, 29 J. Biomed. Mat. Res. 1517–24 (1995). This result was observed with membranes made from a variety of polymers using diverse fabrication methods, including solvent evaporation and stretching. The fact that this behavior was observed for membranes of widely varying chemical composition indicates that microarchitecture, rather than chemistry, is of primary importance in stimulating macrophage migration and neovascularization. Light microscopy revealed that the materials that induce neovascularization have interstices or openings that allow host inflammatory cells, such as monocytes and macrophages, to invade the membrane. Furthermore, once inside the membrane, many of these cells retain a non-flattened morphology and do not adhere to the very thin structural elements of the material. A fibrous capsule overlying the vasculature at the interface may also form around these materials. Brauker observed that materials that produce a thick fibrous capsule without neovascularization at the material-tissue interface had either interstices which were too small for host inflammatory cells to invade, or interstices which were large enough for virtually all of the host cells that invade the membrane to adhere and flatten on the internal structural elements of the material, which provided sufficiently large internal area for cell adhesion. Brauker generally found an increase in inflammatory cell penetration and an increase in vascular structures adjacent to the membrane when the nominal membrane pore size was about 1.0 $\mu$m or larger.

Further, Padera demonstrated that the major events in the process of membrane microarchitecture-driven neovascularization occur within the first week of implantation. Padera, et al., *Time Course of Membrane Microarchitecture-driven Neovascularization*, 17 Biomaterials 277–84 (1996). Host inflammatory cells migrate into the membrane after three days of implantation. Their number increases for seven days, remains constant through 21 days and decreases by roughly half at 329 days. Blood vessels are found closer to the material-tissue interface with increasing time over the first week post-implantation. The vessels first arrive at the interface after three days, increasing rapidly through ten days, and then increase slowly through 21 days. The density of close vascular structures at the interface remained virtually constant after 21 days through 11 months, the duration of Padera's experiment. Fibrous capsule formation starts as early as seven days post-implantation, and the capsule continues to mature until the fibroblasts die or migrate away to leave a nearly acellular, scar-like collagen matrix.

These results correlate with the course of events seen in normal wound healing. In normal wound healing, neutrophils are the predominant cell type at the site of injury within the first 24–48 hours, killing and phagocytosing any bacteria present. The macrophage becomes the predominant cell after this time, removing cellular and foreign debris from the area. Within three to four days, fibroblasts migrate out of the surrounding connective tissue into the wound area and begin to synthesize collagen, which quickly fills the wound space. New blood vessels begin to grow into the area at this time to supply oxygen and nutrients needed by the metabolically active fibroblasts and macrophages in the wound. An important difference between normal wound healing and membrane microarchitecture-driven neovascularization is that in normal wound healing the vessels begin to regress in the second week, but in membrane microarchitecture-driven neovascularization the vessels remain at the interface. Although the mature scar is avascular and acellular in a normal wound, in membrane microarchitecture-driven neovascularization, a multitude of vessels persist at the material-tissue interface in an otherwise largely acellular scar. This persistent adjacent vascular structure would be useful for maintaining the nutrient and oxygen supply to, and thus the viability of, the biological components of artificial organ devices.

These initial experiments which demonstrated the neovascularizing microarchitectural effect used membranes whose surface structure size and spacing were randomly generated, thereby producing an irregular structure. U.S. Pat. No. 5,807,406 describes a microfabricated porous laminar structure for holding living cells composed of net-like layers of polymer with regularly shaped holes. Although these structures are regular within the two dimensional plane of their laminar layers, they are irregular in the third dimensional plane. This creates a less well defined structure in which some interstices are blocked by strands of the polymer net from adjacent layers. Although these structures were also found to generally promote neovascularization at the structure/tissue interface upon implantation into animals, the "blocked" interstices did not allow invasion of those portions of the structure by inflammatory cells.

SUMMARY OF THE INVENTION

Although membranes and layered structures with completely or partially random geometries can exhibit neovascularizing properties, they tend to have areas on their surface comprising interstices which are too small or too large to promote neovascularization. It is desirable that the entire surface of the structure have interstices which allow the invasion of inflammatory cells and promote neovascularization adjacent to the implanted material. It has been discovered that microfabricated, grid-like, three dimensional porous structures are useful in implanted devices to promote adjacent neovascularization and reduce fibroid capsule thickness. The three dimensional porous structures of the invention have well defined, uniform geometries in three dimensions, with a microarchitecture that makes them particularly suitable for implanted device applications.

Among the several objects and features of the present invention may be noted the provision of a porous three dimensional structure suitable for use as a coating or membrane for use in various applications where a reduced thickness of the foreign body capsule and increased neovascularization are desired.

Briefly, apparatus of this invention is a porous three dimensional structure for implantation in a host animal capable of producing an inflammatory foreign body response. The structure comprises first and second layers spaced by a plurality of posts having a predetermined length connecting the first and second layers. Each of the layers has a plurality of openings of a predetermined size permitting fluids and inflammatory cells of the animal to pass through the openings and migrate into an interior volume defined by the first and second layers. The size of the openings and length of the posts promote a non-flattened morphology of the cells. The structure promotes vascularization adjacent to the structure when implanted into the animal.

In another aspect, the structure comprises first and second layers spaced by a spacer connecting the first and second layers. Each of the layers has a plurality of openings of a predetermined size permitting fluids and inflammatory cells of the animal to pass through the openings and migrate into an interior volume defined by the first and second layers. The size of the openings promotes a non-flattened morphology of the cells. The structure promotes vascularization adjacent to the structure when implanted in the animal. Each of the plurality of openings in the first layer is aligned with a corresponding opening of the plurality of openings in the second layer.

In yet another aspect, the invention is also drawn to devices for implantation into an animal which incorporate the three dimensional porous structure of the invention. These devices have at least one exterior surface which comprises the porous three dimensional structure.

In still another aspect, the porous three dimensional structure of the present invention comprises first and second layers spaced by a plurality of posts having a predetermined length connecting the first and second layers. Each of the layers has a plurality of openings of a predetermined size permitting fluids and inflammatory cells of the animal to pass through the openings and migrate into interior cavities defined by the openings in the layers and the posts. Each of the cavities has a volume adapted to promote a non-flattened morphology of the cells. The structure promotes vascularization adjacent to the structure when implanted into the animal.

Other objects and features of the present invention will be in part apparent and in part pointed out hereinafter.

BRIEF DESCRIPTION OF THE DRAWINGS

Corresponding reference characters indicate corresponding parts throughout the several views of the drawings.

DEFINITIONS

"Close vascular structure" or "adjacent vascular structure" as used herein, means a venous or arterial structure which is located not more than one cell layer, and not more than 15 $\mu$m, from the surface of the implanted material.

"Inflammatory cell" as used herein, means a leukocyte associated with the inflammatory response. Monocytes and macrophages are examples of inflammatory cells.

"Non-flattened morphology" as used herein, means that the cell exhibits a generally rounded shape, as opposed to an extended, plate-like, flattened shape. Such morphological distinctions are within the understanding of one of ordinary skill in the biological arts.

DETAILED DESCRIPTION OF THE PREFERRED EMBODIMENT

Figure 1:
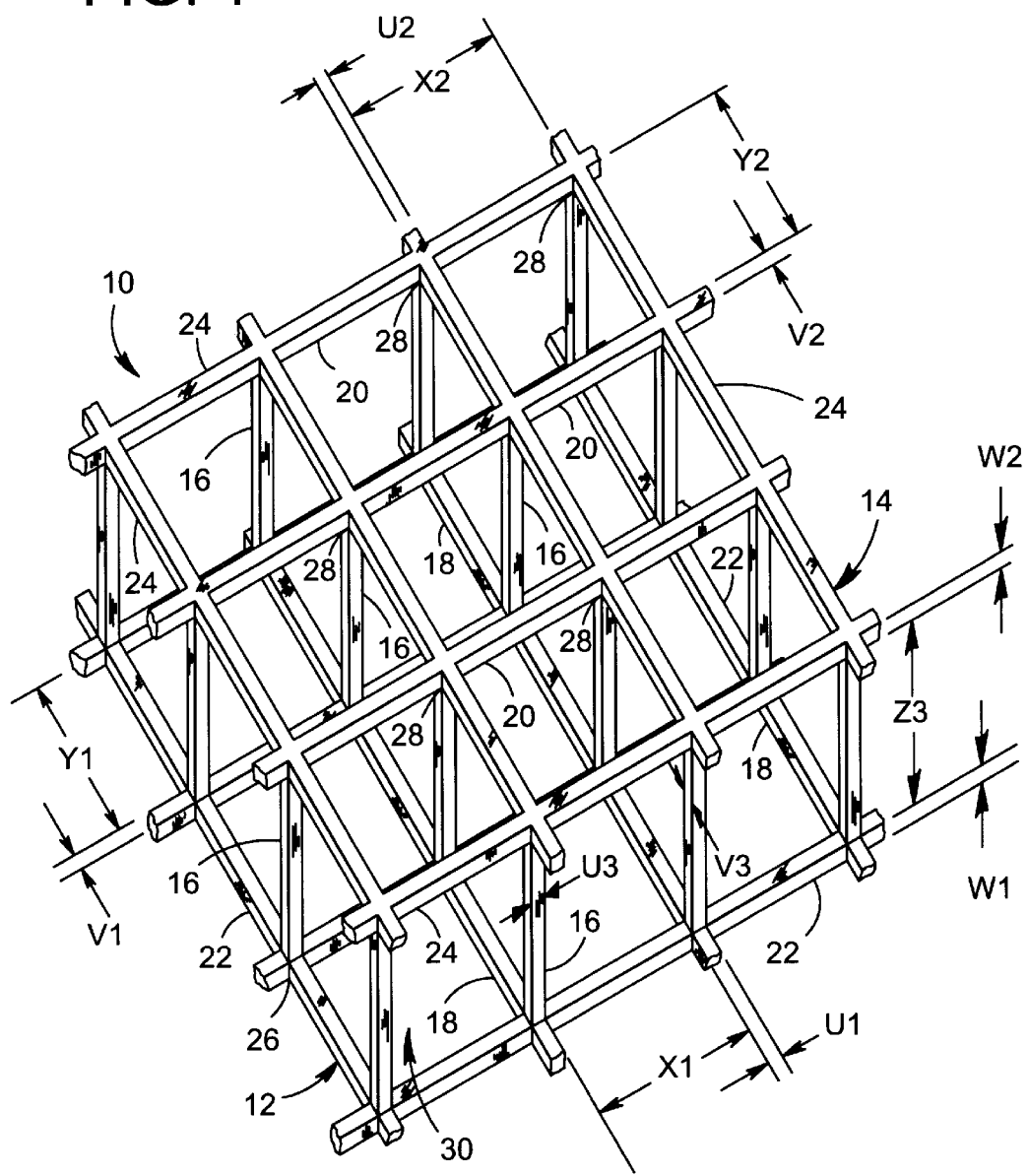
FIG. 1 is a fragmentary perspective of a structure of a first embodiment of the present invention.

Referring now to the drawings and in particular to FIG. 1, a porous three dimensional structure of one embodiment of the present invention for implantation in a host animal is designated in its entirety by the reference numeral 10. Although the structure 10 may have other constructions without departing from the scope of the invention, the structure of the first preferred embodiment has a first layer (generally designated by 12), a second layer (generally designated by 14), and a plurality of posts (or spacers) 16 connecting the first and second layers.

Figure 2:
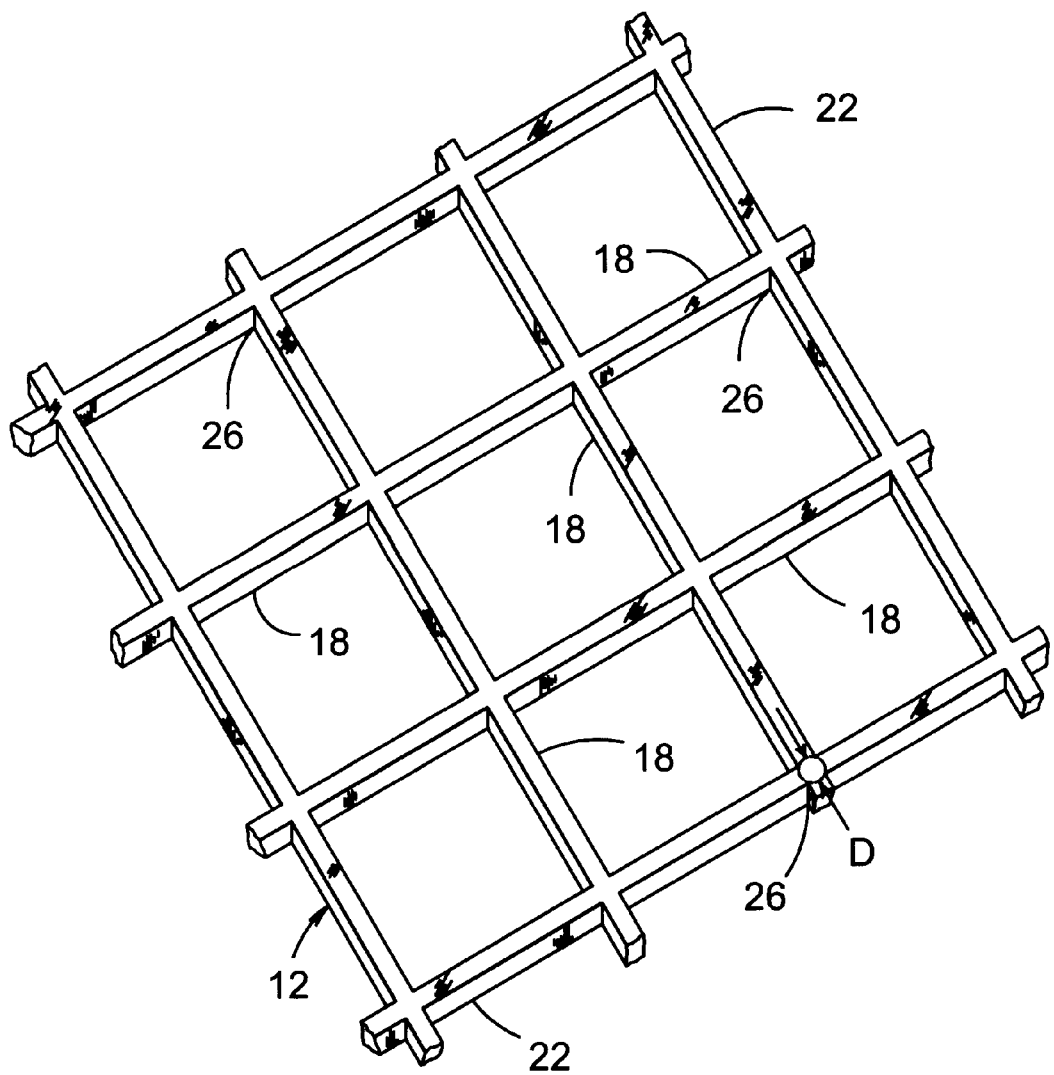
FIG. 2 is a fragmentary perspective of a first layer of the structure.

The first and second layers 12, 14, respectively, have a regular and uniform structure, at least within certain tolerances to be discussed hereinafter. Each layer 12, 14 has a plurality of openings 18, 20, respectively, defined by strands 22, 24, respectively, joined at nodes 26, 28, respectively. As illustrated in FIG. 1, adjoining openings 18, 20 share common nodes 26, 28. Each post 16 extends between one of the nodes 26 of the first layer 12 and one of the nodes 28 of the second layer 14. Preferably, each of the posts 16 extends normal to the first and second layers 12, 14 so the openings 18 in the first layer are aligned with the openings 20 in the second layer and so the aligned openings define prismatic volumes. As will be appreciated by those skilled in the art, each of the posts 16 lies outside these prismatic volumes. As illustrated in FIG. 2, each node 26 (or 28) has an inscribed diameter D less than 5 μm.

As shown in FIG. 1, the openings 18, 20 have a size permitting fluids and inflammatory cells of the animal to pass through the openings and migrate into an interior volume, generally designated by 30, defined by the first and second layers. Although the openings 18, 20 may have other shapes, including uniform shapes and substantially regular polygonal shapes, without departing from the scope of the present invention, the openings 18, 20 of the preferred embodiment are substantially square. Further, the openings 18, 20 of the preferred embodiment are equal in size within certain tolerances to be discussed later.

The openings 18, 20 have minimum widths X1, Y1, X2, Y2 measured between each laterally opposite pair of strands 22, 24 defining the respective openings 18, 20. Although the openings 18, 20 may have other dimensions without departing from the scope of the present invention, the widths X1, Y1, X2, Y2 of the preferred embodiment are generally equal to each other. Further, the widths X1, Y1, X2, Y2 of the preferred embodiment are between about 5 μm and about 20 μm. More preferably, the widths X1, Y1, X2, Y2 are between about 5 μm and about 14 μm, and still more preferably between about 8 μm and about 10 μm. These preferred dimensions have been found to promote non-flattened morphology of invading inflammatory cells, and to promote neovascularization adjacent to the implanted structure, as illustrated in the example provided below.

Although the invention is not bound by any particular theory, it is believed openings of this size allow inflammatory cells invading the structure to adhere to the strands forming the openings in multiple planes. This three-dimensional adherence prevents the cells from assuming a flattened, spread morphology. It is believed this morphological change is an early step in the inflammatory foreign body response cascade. See, for example, DeFife, et al., *Disruption of Filamentous Actin Inhibits Human Macrophage Fusion*, 13 FASEB J. 823–32 (1999). When the non-flattened inflammatory cells remain in the porous structure of the invention, the appearance and persistence of close vascular structures adjacent the implanted material is observed. It is believed the invading inflammatory cells release an angioneogenic signal molecule which encourages the growth or migration of vascular structures close to the implanted structure.

As further illustrated in FIG. 1, the strands 22, 24 of the preferred embodiment have approximately square cross-sectional shapes. Further, the strands 22, 24 have thicknesses (i.e., cross-sectional dimensions) U1, V1, W1, U2, V2, W2 which prevent the flattening of inflammatory cells along the strand. Although other strand thicknesses U1, V1, W1, U2, V2, W2 may be used without departing from the scope of the present invention, the thicknesses of the preferred embodiment are generally equal to each other. Further, the thicknesses U1, V1, W1, U2, V2, W2 of the preferred embodiment are less than about 5 μm. More preferably, the thicknesses U1, V1, W1, U2, V2, W2 are less than about 2 μm, and still more preferably less than about 1 μm. These dimensions are preferred because thickness greater than 5 μm may promote flattening of the inflammatory cells along the strands. Although the invention is not bound by any particular theory, it is believed that strands of a thickness less than 5 μm are not perceived as a continuous surface by the inflammatory cells, and so the cells form non-flattened structures around these strands. In order to be perceived as a discontinuous surface by inflammatory cells, it is preferred that the strands be as thin as possible, while maintaining the mechanical integrity of the structure.

Preferably, each of the posts 16 are equal in length (within the aforementioned tolerances) so the first and second layers 12, 14 are generally planar and generally parallel. Although the posts 16 may have other lengths without departing from the scope of the present invention, the length Z3 of the preferred embodiment is equal to the widths X1, Y1, X2, Y2 of the openings 18, 20 of the preferred embodiment. Thus, the length Z3 is preferably between about 4 μm and about 20 μm. More preferably, the length Z3 is between about 4 μm and about 14 μm, and still more preferably between about 7 μm and about 10 μm.

As further illustrated in FIG. 1, the posts 16 have thicknesses (i.e., cross-sectional dimensions) U3, V3, W3 generally equal to the thicknesses U1, V1, W1, U2, V2, W2 of the strands 22, 24. Thus, the thicknesses U3, V3, W3 of the preferred embodiment are less than about 5 μm. More preferably, the thicknesses U3, V3, W3 are less than about 2 μm, and still more preferably less than about 1 μm.

The size of the openings 18, 20 and length of the posts 16 preferably promote a non-flattened morphology of the cells of interest. For example, it might be beneficial to promote a non-flattened morphology of macrophages having a volume of between about 700 μm³ and about 800 μm³. It is therefore envisioned that the structure might be sized and shaped for supporting the macrophages in a non-flattened morphology. In one potential embodiment for supporting macrophages, the openings 18, 20 and the posts 16 would form individual scaffolds for holding and supporting the cells (i.e., the macrophages). Each scaffold would comprise the strands 22, 24 forming the openings 18, 20 and the posts 16 extending between the corresponding nodes 26, 28 of the openings. It is envisioned that the individual scaffolds might be sized so that the largest ellipsoid which could be held by the scaffold would have a volume of between about 700 μm³ and about 800 μm³. As will be appreciated by those skilled in the art, the largest ellipsoid which could be held by a rectangular prismatic scaffold touches the scaffold at several places (e.g., at four places around each opening). Further, it is envisioned that the sizes of the openings 20, 22 and the lengths of the posts 16 could be selected to create scaffolds shaped so that the largest ellipsoid which could be held by the scaffold would have a maximum dimension less than about four times its minimum dimension. Alternatively, it is envisioned that each scaffold might be sized so that it could hold an ellipsoid having a volume of between about 700 μm³ and about 800 μm³ and a maximum dimension less than about four times its minimum dimension so the ellipsoid touches each of the sides of the corresponding openings. Although the invention is not bound by any particular theory, it is believed that scaffold sizes and shapes within these ranges promote a non-flattened morphology of the macrophages by supporting the cells inside the scaffold.

The porous three dimensional structure 10 described above is made using a photo-lithographic process. A substrate (e.g., a silicon wafer) is coated with a first coat of photosensitive polymer system. For instance, the substrate may be spin coated (e.g., at 4000 rpm for 30 seconds) with a Ciba Geigy adhesion promoter and baked (e.g., at 110° C. for 45 seconds), and spin coated with Ciba Geigy Probimide 412 polymer (e.g., by pre-spinning at 800 rpm, dispensing the polymer for 12 seconds, and spinning at 5800 rpm for 25 seconds) and baked (e.g., at 110° C. for 12 minutes). A first mask (e.g., a conventional glass or quartz grid mask) is placed over the first coat. The masked first coat is exposed to a light source (e.g., 365 nm UV for 10 seconds) and the first coat is developed (e.g., with a Ciba Geigy 3301 developer) to remove unmasked portions of the first coating from the substrate. The first coat is cured such as by vacuum baking the coat at 250° C. for 30 minutes, and cross linked by exposure to 365 nm UV for 50 seconds. The developed first coat forms a first layer 12 having a plurality of openings 18 as illustrated in FIG. 2.

Figure 3:
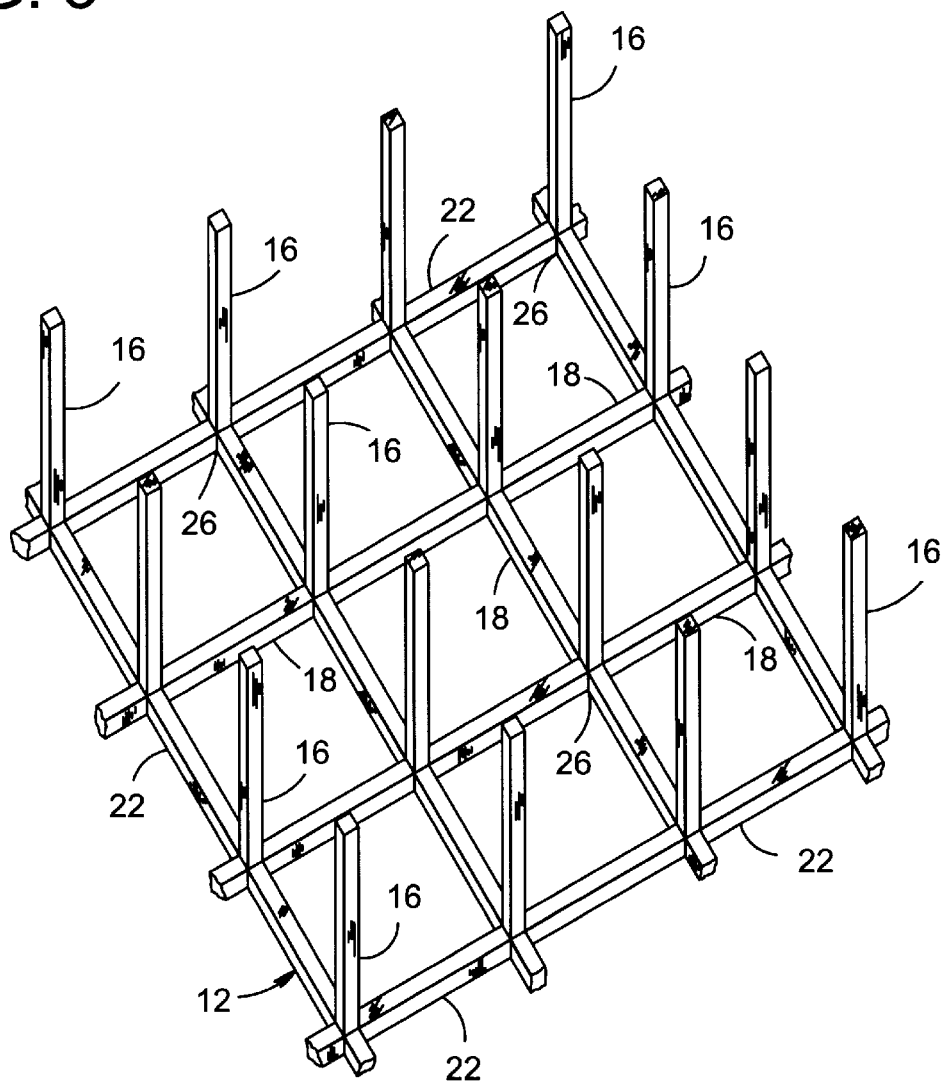
FIG. 3 is a fragmentary perspective of the first layer and a plurality of posts of the structure.

The first layer 12 is coated with a second coat of photosensitive polymer (e.g., by pre-spinning at 2600 rpm and dispensing the polymer for 12 seconds) and baked (e.g., at 110° C. for 12 minutes). A second mask (not shown) is placed over the second coat. It is critical that the second mask be registered with respect to the openings 18 in the first layer 12 so the posts 16 are aligned with the nodes 26 of the first layer. The registration may be accomplished by aligning the mask with markings made in the previous coat outside of the pattern used to make the structure. A microscope and vernier stage may be used to align the mask and manipulate the mask relative to the previous coat. The masked second coat is exposed to the light source (e.g., 365 nm UV at 30 seconds) and developed to remove unmasked portions of the second coat from the first layer 12. The developed second coat is cured (e.g., by vacuum baking at 110° C. for 12 minutes) to form a plurality of posts 16 connected to the first layer 12 as shown in FIG. 3.

The cured second coat is coated with a third coat of photosensitive polymer (not shown) before a third mask (not shown) is placed over the third coat. Preferably, the first and third masks are identical. As with the second mask, it is critical that the third mask is registered with respect to the posts 16 so the nodes 28 of the second layer 14 are aligned with the posts and so the openings 18 of the first layer are aligned with the openings 20 of the second layer. The masked third coat is exposed to the light source (e.g., 365 nm UV for 2.6 seconds) and the exposed third coat is developed to remove unmasked portions of the third coat from the posts 16. The developed third coat is cured (e.g, by vacuum baking at 250° C. for 30 minutes) to form a second layer 14 connected to the posts 16 as shown in FIG. 1. The completed structure may be removed from the substrate using a buffered oxide etchant.

Figure 4:
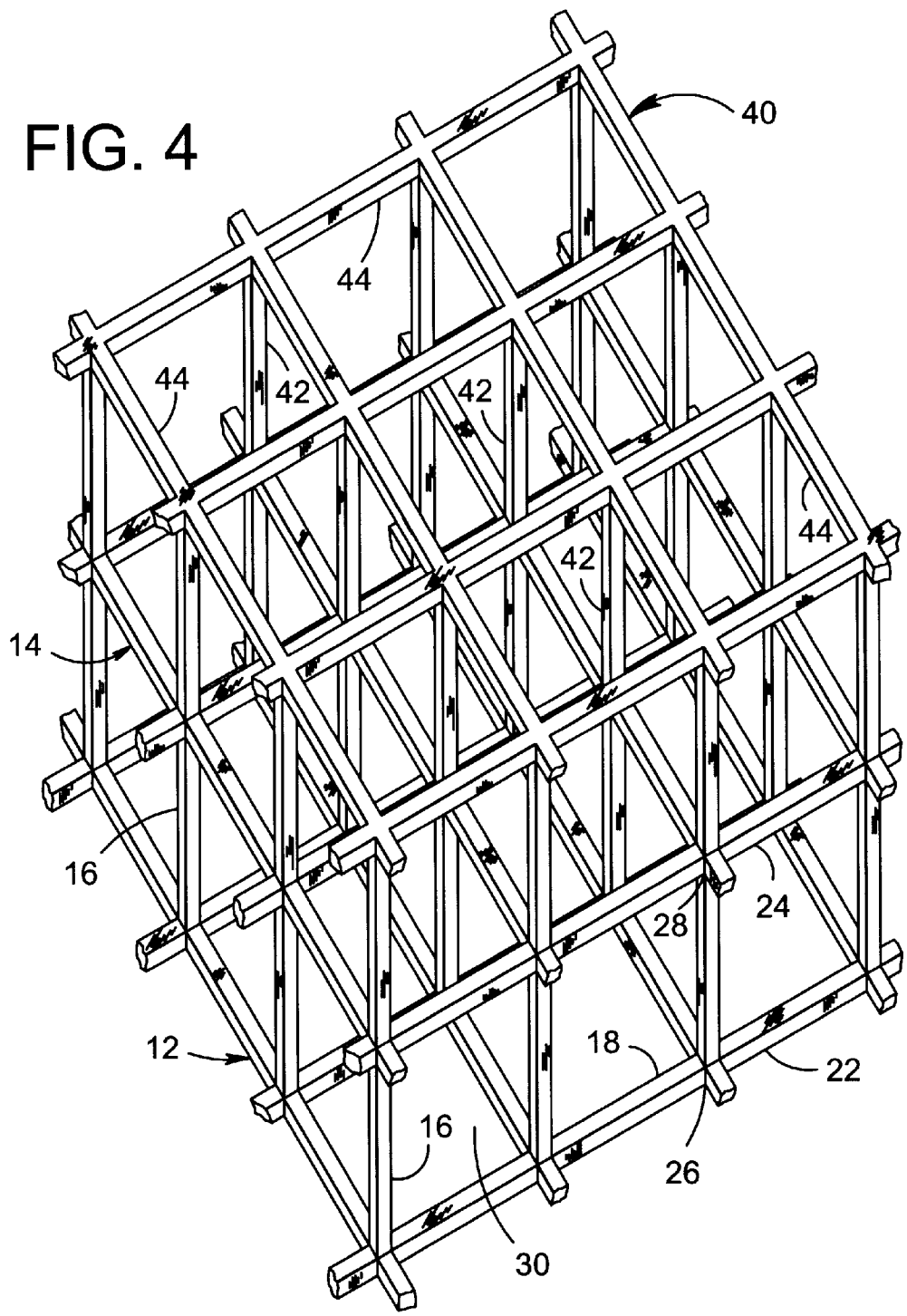
FIG. 4 is a fragmentary perspective of a second embodiment of the present invention having three layers.
Figure 5:
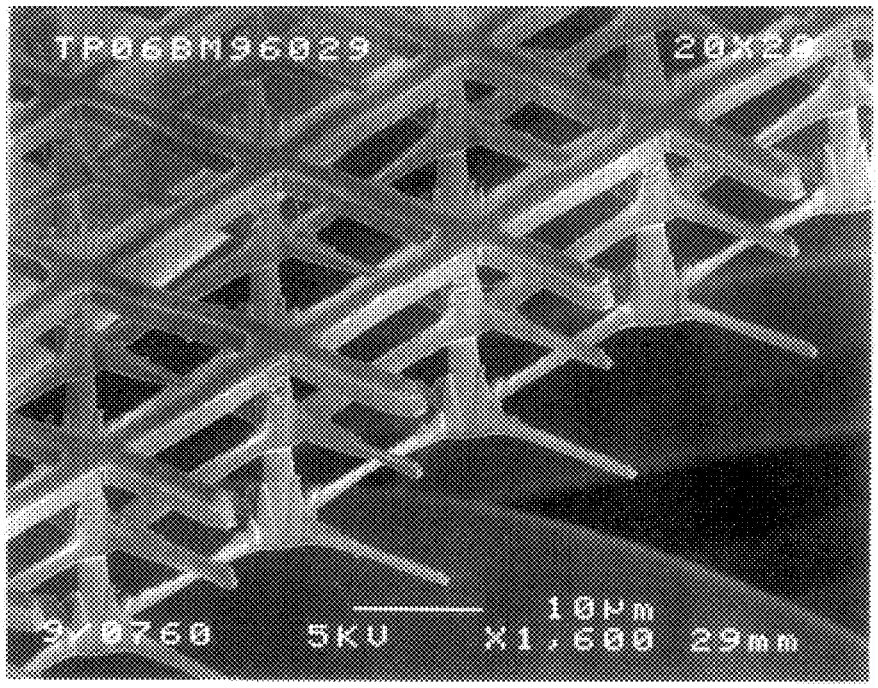
FIG. 5 is an electro-micrograph of a structure of the second embodiment.
Figure 6:
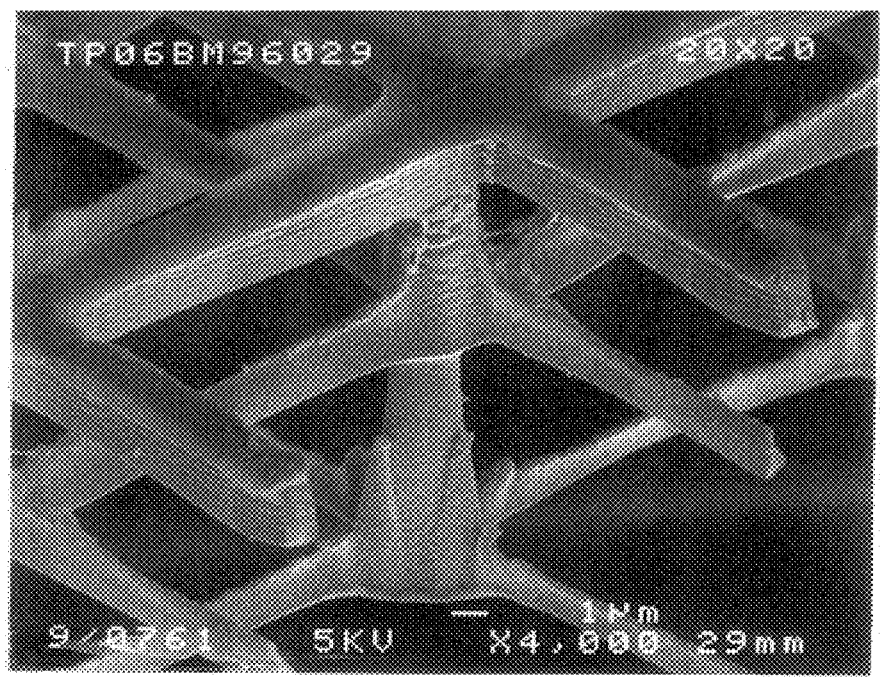
FIG. 6 is an electro-micrograph similar to FIG. 5 but at a higher magnification.

As illustrated in FIG. 4, portions of the previously described method may be repeated to form a structure 10 having a third layer, generally designated by 40, and a second plurality of posts 42. Preferably, the third layer 40 has openings 44 of a size equal to (within certain tolerances) the rest of the openings 18, 20 of the first and second layers 12, 14. Further, the posts 42 preferably have dimensions equal to (within certain tolerances) the dimensions of the posts 16 separating the first and second layers 12, 14.

As used herein, the term "substantially equal" is intended to mean equal within reasonable manufacturing capabilities and preferably having a total tolerance less than about 2 µm, and still more preferably having a total tolerance less than about 1 µm. Thus, strands having substantially equal thicknesses of about 1 µm would more preferably vary in thickness by no more than from about 0.5 µm to about 1.5 µm.

Although the structures shown in FIGS. 1–4 are regular and uniform, those skilled in the art will appreciate that the structures may deviate from these idealized configurations and may have irregularities and non-uniformities without departing from the scope of the present invention. However, in one embodiment the structure varies from these idealized configurations by no more than permitted by the previously discussed manufacturing tolerances.

Several characteristics are desirable for embodiments of the porous three dimensional structure of the present invention, including: 1) biocompatibility; 2) ease of fabrication; 3) an ability to routinely create identifiable, three-dimensional geometries; and 4) chemical inertness and robust mechanical properties. Photosensitive polyimide materials possess all of these characteristics, and are thus a preferred material for making the porous structure 10. In recent studies, polyimide has been used as an implant material with very limited adverse tissue response, indicating its biocompatibility (Haggerty, et al. 107 Acta Otolaryngol (Stockh) 13 (1989)). The method of indirect patterning of non-light sensitive polyimide requires several additional processing steps whereas, processing photoimageable polyimide can be done in the same way as a common negative photoresist, thus greatly facilitating fabrication of the porous structures. After patterning the polyimide film, the area of any flat surface can be identified easily using scanning electron microscopy. Fully cured polyimides have excellent physical and thermal properties including: high tensile strength; a large modulus of elasticity; a high glass transition temperature; and resistance to many acids and organic solvents.

Light sensitive polyimide films suitable for use in the present invention include:

Ultradel® 7501 (U7501) polyimide film: The exact chemical structure of these polyimides from Amoco Chemical Company (Naperville, Ill.) is proprietary. However, it is an inherently light sensitive, preimidized, benzophenone (BTDA) based fluorinated polyimide. The solvent system for this polyimide is gbutyrolactone. Ultradel is a federally registered trademark of Amoco Chemical Company of Chicago, Ill.; and Selectiplast® HTR3-100 (HTR3-100): The HTR3 series of polyimides from OCG Microelectronics (West Paterson, J. J.) are a PMDA/ODA based polyimide which has a sensitizer molecule providing light sensitivity. The exact chemical formulation of the sensitizer molecule is proprietary. The solvent system used for this polyimide is cyclopentanone. Selectiplast is a federally registered trademark of Ciba Geigy Corporation of New York, N.Y.

It should be noted that although photosensitive polyimides are a preferred material for use in making the three dimensional porous structures of the present invention, other micro-fabrication materials with similar characteristics could also be used, including other photosensitive polymers such as those described in U.S. Pat. Nos. 5,994,025, 5,989, 775, 5,985,522, and the like. In addition, etchable polymers or metals such as titanium alloys, cobalt-chromium-molybdenum alloys, cobalt-chromium-tungsten-nickel alloys and non-magnetic stainless steels (300 series stainless steel) may be used. An example of an etchable polymer useful in the present invention is Ultradel® 4212 (U4212). This is an etchable material with a chemical structure of a 4, 4' hexafluoro-isopropylidene-bis pthalic anhydride (HFDA) and 4, 4'-bis(4-aminophenoxy)biphenyl (APBP). The solvent system used for this polyimide is 2-methoxyethylether. If an etchable material, rather than a photosensitive material, is used to make the porous three dimensional structure of the invention, then an etching step must be incorporated into each stage of the production process outlined above. Such a modification is within the ability of one of ordinary skill in the photolithography arts.

As biocompatability of the material is very desirable for uses of the present invention involving prolonged implantation, materials to be used in fabricating embodiments of the present invention for use in implantable devices are preferably tested for biocompatability. The person of ordinary skill in the art can readily evaluate the biocompatability and toxicity of materials in animal models. In addition, the person of ordinary skill in the art would be able to select the proper polymer or other material to use in a particular embodiment of the present invention based on the mechanical properties needed to withstand normal use of that particular embodiment. For instance, an embodiment of the invention which is to be used in an immuno-isolation device for xenotransplant cells, similar to the device described in the example below, could be made from a more rigid material, such as titanum alloy.

The three-dimensional porous structures of the present invention can be incorporated into a variety of devices for implantation into animals capable of producing foreign body responses. Animals in which these devices may be implanted include humans, cats, dogs, horses, cows, chickens, and other animals which may require an implantable surgical device. The three dimensional porous structures of the invention are of particular use in biohybrid, sensor, and drug delivery devices because of the close vascularization promoted by the structures. Close vascularization can aid in providing nutrients and oxygen to the biological component (xeno- or allo-grafted tissues or cells) of biohybrid devices, such as the immuno-isolation device described in U.S. Pat. No. 5,964,804. Close vascularization also allows more accurate readings from indwelling sensors, as the analyte does not have to diffuse through the typical foreign body capsule to reach the sensor. Finally, close vascularization also allows drug-delivery devices to be more effective, as the drug does not have to diffuse over great distances through dense tissues in order to reach the bloodstream.

The following example illustrates various aspects of the present invention:

EXAMPLE

Implantation of Three Dimensional Porous Structures In Vivo

Three dimensional porous structures with square interstices of various sizes were tested by implantation into rats according to the methods described in Brauker, et al., (1995). Porous structures were laminated to nonwoven polyester backing to provide strength for handling. Two 0.8 cm diameter circles of the laminated samples were sealed in a friction-fit ring titanium housing such that the structures were exposed on both sides of the housing. The samples were then sterilized, and implanted into sub-cutaneous pockets created on either side of a midline incision in the backs of Sprague-Dawley rats. After being implanted for three weeks, the samples were retrieved and fixed in 2% glutaraldehyde in Sorensens buffer at pH 7.2. The samples were sectioned perpendicular to the plane of the structure, and stained for light or electron microscopy. The extent of fibrotic encapsulation was characterized, and the number of close vascular structures ("CVS") (e.g., capillaries, arterioles and venules lying at the tissue/implant interface) was determined by microscopic analysis.

Specifically, four different three-layer samples were implanted. Each layer of each sample had substantially square openings having substantially equal minimum widths X, Y as shown in Table 1. The lengths $Z_1$, $Z_2$ of the posts separating the layers varied as shown in Table 1. The table also shows the number of close vascular structures found, the number of sections examined, and the approximate volume ($X \cdot Y \cdot Z_2$) of the cavities of the structure adjacent to the tissue.

TABLE 1

| Sample | X ($\mu$m) | Y ($\mu$m) | $Z_1$ ($\mu$m) | $Z_2$ ($\mu$m) | CVS | Number of Sections | Cavity Volume ($\mu$m$^3$) |
|---|---|---|---|---|---|---|---|
| A | 10 | 10 | 7 | 7 | 21.3 ± 11.6 | 5 | 700 |
| B | 14 | 14 | 7 | 4 | 18.5 ± 3.9 | 9 | 784 |
| C | 14 | 14 | 7 | 7 | 10.6 ± 9.9 | 9 | 1372 |
| D | 20 | 20 | 7 | 7 | 6.6 ± 5.7 | 5 | 2800 |

Sample A demonstrated the greatest number of close vascular structures. Sample B was slightly less effective, while samples C and D were much less effective in stimulating CVS. It is clear that the number of close vascular structures at the surface of the sample correlates with the volume of the cavities exposed to the tissue. Monocytes/macrophages have a modal equivalent volume of about 600 $\mu$m$^3$. It is obvious that macrophages could easily enter the cavities of samples A and B and attach to the structures while maintaining a rounded shape; whereas samples C and D would require considerable flattening of the macrophages for them to anchor themselves within only a portion of the cavity.

In view of the above, it will be seen that the several objects of the invention are achieved and other advantageous results attained.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it intended that all matter contained in the above description or shown in the accompanying drawings shall be interpreted as illustrative and not in a limiting sense.

What is claimed is:

1. A porous three dimensional structure for implantation in a host animal capable of producing an inflammatory foreign body response, the structure comprising first and second layers spaced by a plurality of posts having a predetermined length connecting the first and second layers, each of the layers having a plurality of openings of a predetermined size permitting fluids and inflammatory cells of the animal to pass through the openings and migrate into an interior volume defined by the first and second layers, and wherein the width of each of the plurality of openings is less than about 20 $\mu$m and the size of the openings and length of the posts promote a non-flattened morphology of the cells, and wherein the structure promotes vascularization adjacent to the structure when implanted into the animal.

2. A structure as set forth in claim 1 wherein the plurality of openings in the first layer are substantially equally sized and the plurality of openings in the second layer are substantially equally sized.

3. A structure as set forth in claim 2 wherein each opening of the plurality of openings in the first and second layers has a substantially equal size.

4. A structure as set forth in claim 1 wherein each opening of the plurality of openings has a minimum width of between about 5 $\mu$m and about 20 $\mu$m.

5. A structure as set forth in claim 4 wherein the minimum width of each opening of the plurality of openings is between about 5 $\mu$m and about 14 $\mu$m.

6. A structure as set forth in claim 5 wherein the minimum width of each opening of the plurality of openings is between about 8 µm and about 10 µm.

7. A structure as set forth in claim 1 wherein each opening of the plurality of openings in the first and second layers has a substantially uniform shape.

8. A structure as set forth in claim 7 wherein the shape of each opening of the plurality of openings in the first and second layers is a substantially regular polygonal shape.

9. A structure as set forth in claim 8 wherein the shape of each opening of the plurality of openings in the first and second layers is substantially square.

10. A structure as set forth in claim 9 wherein each opening of the plurality of openings in the first and second layers has four sides of substantially equal length, and each of the posts has a length substantially equal to the length of the sides of the openings.

11. A structure as set forth in claim 1 wherein each of the first and second layers has a thickness of less than about 5 µm.

12. A structure as set forth in claim 11 wherein the thickness of the first and second layers is less than about 2 µm.

13. A structure as set forth in claim 12 wherein the thickness of the first and second layers is less than about 1 µm.

14. A structure as set forth in claim 1 wherein each opening of the plurality of openings in the first and second layers is separated from adjacent openings of the plurality of openings by a strand having maximum cross sectional dimension of less than about 5 µm.

15. A structure as set forth in claim 14 wherein the maximum cross section dimension of each strand is less than about 2 µm.

16. A structure as set forth in claim 15 wherein the maximum cross section dimension of each strand is less than about 1 µm.

17. A structure as set forth in claim 14 wherein each strand has a substantially square cross-sectional shape.

18. A structure as set forth in claim 1 wherein each post of the plurality of posts has a thickness of less than about 5 µm.

19. A structure as set forth in claim 18 wherein the thickness of each post of the plurality of posts is less than about 2 µm.

20. A structure as set forth in claim 19 wherein the thickness of each post of the plurality of posts is less than about 1 µm.

21. A structure as set forth in claim 1 wherein each post of the plurality of posts has a substantially square cross-sectional shape.

22. A structure as set forth in claim 1 wherein each post of the plurality of posts has a length of between about 4 µm and about 20 µm.

23. A structure as set forth in claim 22 wherein the length of each post of the plurality of posts is between about 4 µm and about 14 µm.

24. A structure as set forth in claim 23 wherein the length of each post of the plurality of posts is between about 7 µm and about 10 µm.

25. A structure as set forth in claim 1 wherein the first and second layers are generally planar and generally parallel.

26. A structure as set forth in claim 1 wherein groups of openings within the plurality of openings of the first layer share common nodes, groups of openings within the plurality of openings of the second layer share common nodes, and each of the posts of the plurality of posts extends between one of the nodes of the first layer and one of the nodes of the second layer.

27. A structure as set forth in claim 26 wherein each of the nodes has an inscribed diameter of less than about 5 µm.

28. A structure as set forth in claim 26 wherein a post is located at substantially all of the nodes.

29. A structure as set forth in claim 1 wherein the plurality of posts is a first plurality of posts and the structure further comprises a third layer and a second plurality of posts having a predetermined length connecting the second and third layers, the third layer having a plurality of openings of a predetermined size permitting fluids and inflammatory cells of the animal to pass through each opening of the plurality of openings in the third layer and migrate into an interior volume defined by the second and third layers, and wherein the size of the openings in the third layer and length of each post of the second plurality of posts promote a non-flattened morphology of the cells, and wherein the structure promotes vascularization adjacent the structure when implanted in the animal.

30. A device for implantation into an animal in which at least one exterior surface of the device comprises the porous three dimensional structure recited in claim 29.

31. A device for implantation into an animal in which at least one exterior surface of the device comprises the porous three dimensional structure recited in claim 1.

32. A structure as set forth in claim 1 wherein each post of the plurality of posts extends normal to the first and second layers.

33. A structure as set forth in claim 1 wherein the first and second layers and the plurality of posts are made of a polyimide.

34. A porous three dimensional structure for implantation in a host animal capable of producing an inflammatory foreign body response, the structure comprising first and second layers spaced by a spacer connecting the first and second layers, each of the layers having a plurality of openings of a predetermined size permitting fluids and inflammatory cells of the animal to pass through the openings and migrate into an interior volume defined by the first and second layers, wherein the width of each of the plurality of openings is less than about 20 µm and the size of the openings promote a non-flattened morphology of the cells, and wherein the structure promotes vascularization adjacent to the structure when implanted in the animal, and wherein each of the plurality of openings in the first layer is aligned with a corresponding opening of the plurality of openings in the second layer.

35. A structure as set forth in claim 34 wherein each pair of aligned openings in the first and second layers defines a prismatic volume and the spacer lies outside each of the prismatic volumes.

36. A device for implantation into an animal in which at least one exterior surface of the device comprises the porous three dimensional structure recited in claim 34.

37. A porous three dimensional structure for implantation in a host animal capable of producing an inflammatory foreign body response, the structure comprising first and second layers spaced by a plurality of posts having a predetermined length connecting the first and second layers, each of the layers having a plurality of openings of a predetermined size permitting fluids and inflammatory cells of the animal to pass through the openings and migrate into interior scaffolds defined by said openings and said plurality of posts, and wherein the width of each of the plurality of openings is less than about 20 µm and each of said scaffolds is sized and shaped to promote a non-flattened morphology of the cells, and wherein the structure promotes vascularization adjacent to the structure when implanted into the animal.

38. A structure as set forth in claim 37 wherein each of said scaffolds is sized so that the largest ellipsoid which can be held by the scaffold has a volume of between about 700 $\mu m^3$ and about 800 $\mu m^3$.

39. A structure as set forth in claim 38 wherein each of said scaffolds is shaped so that the largest ellipsoid which can be held by the scaffold has a maximum dimension less than about four times a minimum dimension of the ellipsoid.

40. A structure as set forth in claim 37 wherein each of said scaffolds is shaped so that the largest ellipsoid which can be held by the scaffold has a maximum dimension less than about four times a minimum dimension of the ellipsoid.

41. A structure as set forth in claim 37 wherein each of said plurality of openings in each layer has a plurality of sides.

42. A structure as set forth in claim 41 wherein each of said scaffolds is sized so that an ellipsoid which can be held by the scaffold so the ellipsoid touches each of said plurality of sides of corresponding openings in said layers has a volume of between about 700 $\mu m^3$ and about 800 $\mu m^3$.

43. A structure as set forth in claim 42 wherein each of said scaffolds is shaped so that the ellipsoid which can be held by the scaffold so the ellipsoid touches each of said plurality of sides of corresponding openings in said layers has a maximum dimension less than about four times its minimum dimension.

44. A structure as set forth in claim 41 wherein each of said scaffolds is shaped so that the ellipsoid which can be held by the scaffold so the ellipsoid touches each of said plurality of sides of corresponding openings in said layers has a maximum dimension less than about four times a minimum dimension of the ellipsoid.

\* \* \* \* \*